United States Patent [19]

Stetter et al.

[11] 4,385,069
[45] May 24, 1983

[54] COMBATING FUNGI WITH N-ALLENYL-ACETANILIDES

[75] Inventors: Jörg Stetter; Winfried Lunkenheimer, both of Wuppertal; Wilhelm Brandes, Leichlingen, all of Fed. Rep. of Germany

[73] Assignee: Bayer Aktiengesellschaft, Leverkusen, Fed. Rep. of Germany

[21] Appl. No.: 136,026

[22] Filed: Mar. 31, 1980

[30] Foreign Application Priority Data

Apr. 25, 1979 [DE] Fed. Rep. of Germany ....... 2916692

[51] Int. Cl.³ .................... A01N 37/22; A01N 37/24; C07C 103/365; C07C 103/58
[52] U.S. Cl. .............................. 424/324; 260/465 D; 260/454; 260/455 A; 260/456 A; 424/269; 424/273 R; 424/273 P; 424/272; 424/282; 424/285; 424/286; 424/302; 424/301; 424/303; 424/304; 424/309; 548/248; 548/262; 548/341; 548/377; 549/77; 549/419; 549/487; 560/24; 560/30; 560/43; 564/192; 564/202; 564/207; 564/214; 564/218
[58] Field of Search ................ 548/262, 341; 564/192, 564/202, 214, 209, 218; 424/269, 324, 302, 304

[56] References Cited

U.S. PATENT DOCUMENTS

| 3,780,090 | 12/1973 | Akiba et al. | 560/43 |
|---|---|---|---|
| 4,021,224 | 5/1977 | Pallos et al. | 71/88 |
| 4,151,295 | 4/1979 | Hubele | 564/202 |
| 4,275,079 | 6/1981 | Dorn | 564/207 |
| 4,325,966 | 4/1982 | Funja | 564/202 |

FOREIGN PATENT DOCUMENTS 2350944  4/1974  Fed. Rep. of Germany ...... 424/304

OTHER PUBLICATIONS

Overman et al, Tetrahedron Letters, No. 7, Feb. 1979, pp. 559, 600.

T. R. Melikyan et al, Chemical Abstracts, vol. 89, Abstract No. 75356s, p. 405.

*Primary Examiner*—Alton D. Rollins
*Attorney, Agent, or Firm*—Sprung, Horn, Kramer & Woods

[57] ABSTRACT

N-allenyl-acetanilides of the formula

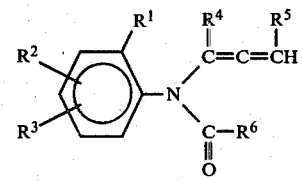

in which
$R^1$ represents hydrogen, alkyl or halogen,
$R^2$ represents hydrogen or alkyl,
$R^3$ represents hydrogen or alkyl,
$R^4$ represents hydrogen or alkyl,
$R^5$ represents hydrogen or alkyl and
$R^6$ represents furyl, tetrahydrofuryl, thiophenyl or tetrahydrothiophenyl; isoxazolyl which is optionally substituted by alkyl; alkyl, alkenyl or alkynyl, in each case optionally substituted by cyano or thiocyano; dihalogenoalkyl; or the grouping $-CH_2-Az$, $-CH_2-OR^7$, $-OR^7$ $-SR^7$, $-CH_2-OSO_2R^7$, $-COOR^7$ or

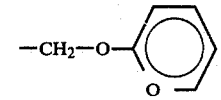

wherein
$R^7$ represents an optionally substituted alkyl, alkenyl, alkynyl or alkoxyalkyl radical and Az represents pyrazol-1-yl, 1,2,4-triazol-1-yl or imidazol-1-yl.

which possess fungicidal properties.

6 Claims, No Drawings

COMBATING FUNGI WITH N-ALLENYL-ACETANILIDES

The present invention relates to certain new N-allenyl-acetanilides, to a process for their preparation and to their use as fungicides.

It has already been disclosed that such halogenoacetanilides as, for example, N-chloroacetyl-N-(2,6-dialkylphenyl)-alanine alkyl esters and -glycine alkyl esters can be employed with good success for combating fungal diseases of plants (see DI-OS (German Published Specification) No. 2,350,944 and U.S. Pat. No. 3,780,090). However, their action is not always completely satisfactory, especially when small amounts and low concentrations are used and in particular also when combating Phytophthora species.

The present invention now provides, as new compounds, the N-allenyl-acetanilides of the general formula

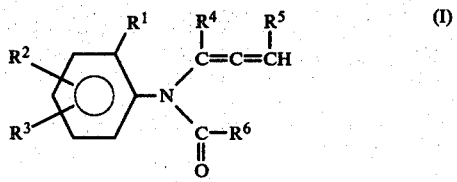

in which
R¹ represents hydrogen, alkyl or halogen,
R² represents hydrogen or alkyl,
R₃ represents hydrogen or alkyl,
R⁴ represents hydrogen or alkyl,
R⁵ represents hydrogen or alkyl and
R⁶ represents furyl, tetrahydrofuryl, thiophenyl or tetrahydrothiophenyl; isoxazolyl which is optionally substituted by alkyl; alkyl, alkenyl or alkynyl, in each case optionally substituted by cyano or thiocyano; dihalogenoalkyl; or the grouping —CH₂—Az, —CH₂—OR⁷, —CH₂—SR⁷, —OR⁷, —SR⁷, —CH₂—OSO₂R⁷, —COOR⁷,

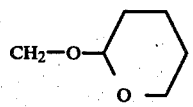

or —CH₂—SR⁷,
wherein
R⁷ represents an optionally substituted alkyl, alkenyl, alkynyl or alkoxyalkyl radical and Az represents pyrazol-1-yl, 1,2,4-triazol-1-yl or imidazol-1-yl.

It has been found that the N-allenyl-acetanilides of the formula (I) have powerful fungicidal properties. Surprisingly, the compounds according to the invention exhibit a considerably higher action, especially against Phytophthora, than the N-chloroacetyl-N-(2,6-dialkylphenyl)-alanine alkyl esters and -glycine alkyl esters known from the state of the art.

Preferred compounds of the formula (I) are those in which R², R³, R⁴ and R⁵ are selected independently and each represent hydrogen or straight-chain or branched alkyl with 1 to 4 carbon atoms;
R¹ represents hydrogen, straight-chain or branched alkyl with 1 to 4 carbon atoms or halogen (especially fluorine, chlorine or bromine),
R⁶ represents furyl, tetrahydrofuryl, thiophenyl, tetrahydrothiophenyl; isoxazolyl which is optionally substituted by methyl or ethyl; alkyl with 1 to 4 carbon atoms or alkenyl or alkynyl with in either case 2 to 4 carbon atoms, in each case optionally substituted by cyano or thiocyano; dihalogenoalkyl with 1 to 2 carbon atoms (preferred halogen atoms being fluorine and chlorine); or the grouping —CH₂—Az, —CH₂—OR⁷, —CH₂—SR⁷, —OR⁷, —SR⁷, —CH₂—OSO₂R⁷, —COOR⁷ or

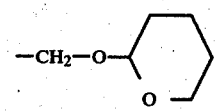

Az represents pyrazol-1-yl, 1,2,4-triazol-1-yl or imidazol-1-yl; and
R⁷ represents alkyl with 1 to 4 carbon atoms or alkenyl or alkynyl with in either case 2 to 4 carbo atoms, in each case optionally substituted by halogen (especially fluorine, chlorine or bromine), cyano or thiocyano, or represents alkoxyalkyl with 1 to 4 carbon atoms in each alkyl part.

Those substituted N-propargyl-anilines of the formula (I) are very particularly preferred in which R¹ represents hydrogen, methyl, ethyl, isopropyl, sec.-butyl, tert.-butyl, chlorine or bromine; R² and R³ represent hydrogen, methyl, ethyl, isopropyl, sec.-butyl or tert.-butyl; R⁴ and R⁵ represent hydrogen, methyl or ethyl; and R⁶ represents 2-furyl, 2-thienyl, 2-tetrahydrofuryl, vinyl, 5-methylisoxazol-3-yl, methoxymethyl, ethoxymethyl, allyloxymethyl, propargyloxymethyl, ethoxymethoxymethyl, methylmercaptomethyl, methoxy, ethoxy, methylmercapto, methylsulphonyloxymethyl, methoxycarbonyl, ethoxycarbonyl, propargyloxycarbonyl, dichloromethyl, pyrazol-1-yl-methyl, imidazol-1-yl-methyl, 1,2,4-triazol-1-yl-methyl or tetrahydropyran-2-yl-oxymethyl.

The following compounds of the general formula (I) may be mentioned specifically, in addition to the compounds mentioned later in the preparative examples:

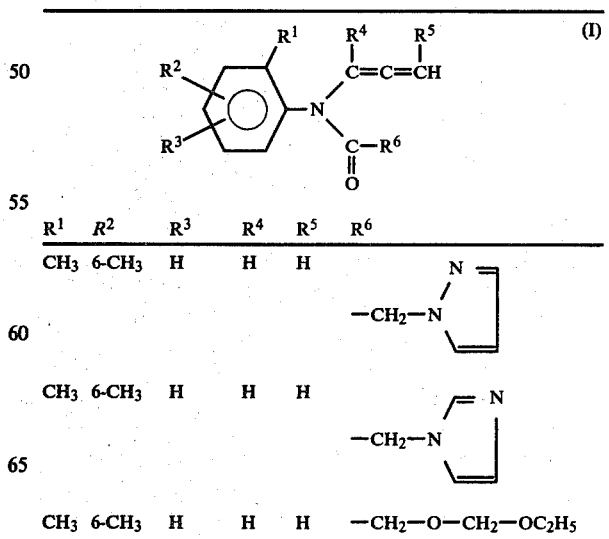

| R¹ | R² | R³ | R⁴ | R⁵ | R⁶ |
|---|---|---|---|---|---|
| CH₃ | 6-CH₃ | H | H | H | —CH₂—N(pyrazolyl) |
| CH₃ | 6-CH₃ | H | H | H | —CH₂—N(imidazolyl) |
| CH₃ | 6-CH₃ | H | H | H | —CH₂—O—CH₂—OC₂H₅ |

-continued $$\begin{array}{c} R^1 \\ R^2 \diagdown \diagup R^4 \diagup R^5 \\ \phantom{R^2}\big|\phantom{xx}C=CH \\ \text{Ar-N} \\ \phantom{xxx}| \\ R^3 \phantom{xx} C=O \\ \phantom{xxxxx}R^6 \end{array}$$ (I)

| $R^1$ | $R^2$ | $R^3$ | $R^4$ | $R^5$ | $R^6$ |
|---|---|---|---|---|---|
| CH₃ | 6-CH₃ | H | H | H | —CH₂—O—(tetrahydropyran-2-yl) |
| CH₃ | 6-CH₃ | H | H | H | (tetrahydrofuran-2-yl) |
| CH₃ | 6-CH₃ | H | H | H | (thiophen-2-yl) |
| CH₃ | 6-CH₃ | H | H | H | (tetrahydrothiophen-2-yl) |
| CH₃ | 6-CH₃ | H | H | H | —CH₂—S—CH₃ |
| CH₃ | 6-CH₃ | H | H | H | —CH₂—S—C₂H₅ |
| CH₃ | 6-CH₃ | H | H | H | —CHCl₂ |
| CH₃ | 6-CH₃ | H | H | H | —COOCH₃ |
| CH₃ | 6-CH₃ | H | H | H | —CH₂—O—SO₂CH₃ |
| CH₃ | 6-CH₃ | H | H | H | —CO—O—CH₂—C≡CH |
| CH₃ | 6-CH₃ | H | H | H | —CH=CH₂ |
| CH₃ | 6-CH₃ | H | CH₃ | H | (furan-2-yl) |
| CH₃ | 6-CH₃ | H | CH₃ | H | —CH₂—O—CH₃ |
| CH₃ | 6-CH₃ | H | CH₃ | H | —CH₂—N(1,2,4-triazol-1-yl) |
| CH₃ | 6-CH₃ | H | CH₃ | H | —CH₂—N(pyrazol-1-yl) |
| CH₃ | 6-CH₃ | H | CH₃ | H | —CH₂—N(imidazol-1-yl) |
| CH₃ | 6-CH₃ | H | CH₃ | H | —CH₂—OC₂H₅ |
| CH₃ | 6-CH₃ | H | CH₃ | H | —CH₂—O—CH₂—OC₂H₅ |
| CH₃ | 6-CH₃ | H | CH₃ | H | —CH₂—O—(tetrahydropyran-2-yl) |
| CH₃ | 6-CH₃ | H | CH₃ | H | (tetrahydrofuran-2-yl) |
| CH₃ | 6-CH₃ | H | CH₃ | H | (thiophen-2-yl) |
| CH₃ | 6-CH₃ | H | CH₃ | H | (tetrahydrothiophen-2-yl) |
| CH₃ | 6-CH₃ | H | CH₃ | H | —CH₂—S—CH₃ |
| CH₃ | 6-CH₃ | H | CH₃ | H | —CH₂—S—C₂H₅ |
| CH₃ | 6-CH₃ | H | CH₃ | H | —CHCl₂ |
| CH₃ | 6-CH₃ | H | CH₃ | H | —COOCH₃ |
| CH₃ | 6-CH₃ | H | CH₃ | H | —CH₂—O—SO₂CH₃ |
| CH₃ | 6-CH₃ | H | CH₃ | H | —CO—OCH₂—C≡CH |
| CH₃ | 6-CH₃ | H | CH₃ | H | —CH=CH₂ |
| CH₃ | 6-CH₃ | H | H | CH₃ | (furan-2-yl) |
| CH₃ | 6-CH₃ | H | H | CH₃ | —CH₂—OCH₃ |
| CH₃ | 6-CH₃ | H | H | CH₃ | —CH₂—N(1,2,4-triazol-1-yl) |
| CH₃ | 6-CH₃ | H | H | CH₃ | —CH₂—N(pyrazol-1-yl) |
| CH₃ | 6-CH₃ | H | H | CH₃ | —CH₂—N(imidazol-1-yl) |
| CH₃ | 6-CH₃ | H | H | CH₃ | —CH₂—OC₂H₅ |
| CH₃ | 6-CH₃ | H | H | CH₃ | —CH₂—O—CH₂—OC₂H₅ |
| CH₃ | 6-CH₃ | H | H | CH₃ | —CH₂—O—(tetrahydropyran-2-yl) |
| CH₃ | 6-CH₃ | H | H | CH₃ | (tetrahydrofuran-2-yl) |
| CH₃ | 6-CH₃ | H | H | CH₃ | (thiophen-2-yl) |
| CH₃ | 6-CH₃ | H | H | CH₃ | (tetrahydrothiophen-2-yl) |
| CH₃ | 6-CH₃ | H | H | CH₃ | —CH₂—SCH₃ |
| CH₃ | 6-CH₃ | H | H | CH₃ | —CH₂—SC₂H₅ |

-continued $$\text{(I)}$$

Structure (I): phenyl ring bearing $R^1$, $R^2$, $R^3$ substituents; the ring carbon bears an N which is substituted by $-C(R^4)=C(R^5)=CH$ (allenyl) and $-C(O)-R^6$.

| $R^1$ | $R^2$ | $R^3$ | $R^4$ | $R^5$ | $R^6$ |
|---|---|---|---|---|---|
| CH₃ | 6-CH₃ | H | H | CH₃ | —CHCl₂ |
| CH₃ | 6-CH₃ | H | H | CH₃ | —COOCH₃ |
| CH₃ | 6-CH₃ | H | H | CH₃ | —CH₂—O—SO₂CH₃ |
| CH₃ | 6-CH₃ | H | H | CH₃ | —CO—O—CH₂—C≡CH |
| CH₃ | 6-CH₃ | H | H | CH₃ | —CH=CH₂ |
| CH₃ | 6-CH₃ | H | CH₃ | CH₃ | 2-furyl |
| CH₃ | 6-CH₃ | H | CH₃ | CH₃ | —CH₂—OCH₃ |
| CH₃ | 6-CH₃ | H | CH₃ | CH₃ | —CH₂—N(1,2,4-triazol-1-yl) |
| CH₃ | 6-CH₃ | H | CH₃ | CH₃ | —CH₂—N(pyrazol-1-yl) |
| CH₃ | 6-CH₃ | H | CH₃ | CH₃ | —CH₂—N(imidazol-1-yl) |
| CH₃ | 6-CH₃ | H | CH₃ | CH₃ | —CH₂—OC₂H₅ |
| CH₃ | 6-CH₃ | H | CH₃ | CH₃ | —CH₂—O—CH₂—OC₂H₅ |
| CH₃ | 6-CH₃ | H | CH₃ | CH₃ | —CH₂—O—(tetrahydropyran-2-yl) |
| CH₃ | 6-CH₃ | H | CH₃ | CH₃ | 2-tetrahydrofuryl |
| CH₃ | 6-CH₃ | H | CH₃ | CH₃ | 2-thienyl |
| CH₃ | 6-CH₃ | H | CH₃ | CH₃ | 2-tetrahydrothienyl |
| CH₃ | 6-CH₃ | H | CH₃ | CH₃ | —CH₂—SCH₃ |
| CH₃ | 6-CH₃ | H | CH₃ | CH₃ | —CH₂—SC₂H₅ |
| CH₃ | 6-CH₃ | H | CH₃ | CH₃ | —CHCl₂ |
| CH₃ | 6-CH₃ | H | CH₃ | CH₃ | —COOCH₃ |
| CH₃ | 6-CH₃ | H | CH₃ | CH₃ | —CH₂—O—SO₂CH₃ |
| CH₃ | 6-CH₃ | H | CH₃ | CH₃ | —CO—O—CH₂—C≡CH |
| CH₃ | 6-CH₃ | H | CH₃ | CH₃ | —CH=CH₂ |
| CH₃ | 6-C₂H₅ | H | H | H | 2-furyl |
| CH₃ | 6-C₂H₅ | H | H | H | —CH₂—OCH₃ |
| CH₃ | 6-C₂H₅ | H | H | H | —CH₂—N(1,2,4-triazol-1-yl) |
| CH₃ | 6-C₂H₅ | H | H | H | —CH₂—N(pyrazol-1-yl) |
| CH₃ | 6-C₂H₅ | H | H | H | —CH₂—O—C₂H₅ |
| CH₃ | 6-C₂H₅ | H | H | H | —CH₂—O—SO₂CH₃ |
| CH₃ | 6-C₂H₅ | H | H | H | —CHCl₂ |
| CH₃ | 6-C₂H₅ | H | H | H | —COOCH₃ |
| CH₃ | 6-C₂H₅ | H | H | H | 2-tetrahydrofuryl |
| CH₃ | 6-C₂H₅ | H | H | H | —CH₂—SCH₃ |
| CH₃ | 6-C₂H₅ | H | H | H | —CH₂—O—(tetrahydropyran-2-yl) |
| CH₃ | 6-C₂H₅ | H | H | H | —CH=CH₂ |
| CH₃ | 6-C₂H₅ | H | CH₃ | H | 2-furyl |
| CH₃ | 6-C₂H₅ | H | CH₃ | H | —CH₂—OCH₃ |
| CH₃ | 6-C₂H₅ | H | CH₃ | H | —CH₂—N(1,2,4-triazol-1-yl) |
| CH₃ | 6-C₂H₅ | H | CH₃ | H | —CH₂—N(pyrazol-1-yl) |
| CH₃ | 6-C₂H₅ | H | CH₃ | H | —CH₂—O—C₂H₅ |
| CH₃ | 6-C₂H₅ | H | CH₃ | H | —CH₂—O—SO₂CH₃ |
| CH₃ | 6-C₂H₅ | H | CH₃ | H | —CHCl₂ |
| CH₃ | 6-C₂H₅ | H | CH₃ | H | —COOCH₃ |
| CH₃ | 6-C₂H₅ | H | CH₃ | H | 2-tetrahydrofuryl |
| CH₃ | 6-C₂H₅ | H | CH₃ | H | —CH₂—SCH₃ |
| CH₃ | 6-C₂H₅ | H | CH₃ | H | —CH₂—O—(tetrahydropyran-2-yl) |
| CH₃ | 6-C₂H₅ | H | CH₃ | H | —CH=CH₂ |

-continued

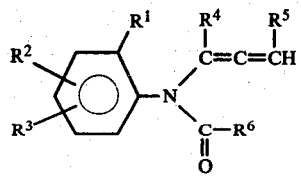

| R¹ | R² | R³ | R⁴ | R⁵ | R⁶ |
|---|---|---|---|---|---|
| CH₃ | 6-C₂H₅ | H | H | CH₃ | 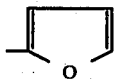 |
| CH₃ | 6-C₂H₅ | H | H | CH₃ | —CH₂—OCH₃ |
| CH₃ | 6-C₂H₅ | H | H | CH₃ | 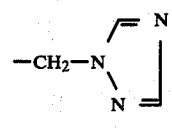 |
| CH₃ | 6-C₂H₅ | H | H | CH₃ | 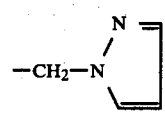 |
| CH₃ | 6-C₂H₅ | H | H | CH₃ | —CH₂—O—C₂H₅ |
| CH₃ | 6-C₂H₅ | H | H | CH₃ | —CH₂—O—SO₂CH₃ |
| CH₃ | 6-C₂H₅ | H | H | CH₃ | —CHCl₂ |
| CH₃ | 6-C₂H₅ | H | H | CH₃ | —COOCH₃ |
| CH₃ | 6-C₂H₅ | H | H | CH₃ | 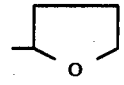 |
| CH₃ | 6-C₂H₅ | H | H | CH₃ | —CH₂—SCH₃ |
| CH₃ | 6-C₂H₅ | H | H | CH₃ | 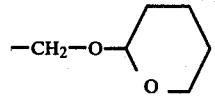 |
| CH₃ | 6-C₂H₅ | H | H | CH₃ | —CH=CH₂ |
| C₂H₅ | 6-C₂H₅ | H | H | H | 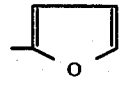 |
| C₂H₅ | 6-C₂H₅ | H | H | H | —CH₂—OCH₃ |
| C₂H₅ | 6-C₂H₅ | H | H | H | 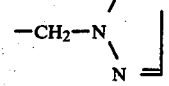 |
| C₂H₅ | 6-C₂H₅ | H | H | H | 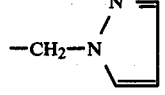 |
| C₂H₅ | 6-C₂H₅ | H | H | H | —CH₂—O—C₂H₅ |
| C₂H₅ | 6-C₂H₅ | H | H | H | —CH₂—O—SO₂CH₃ |
| C₂H₅ | 6-C₂H₅ | H | H | H | —CHCl₂ |
| C₂H₅ | 6-C₂H₅ | H | H | H | —COOCH₃ |
| C₂H₅ | 6-C₂H₅ | H | H | H | 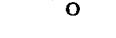 |
| C₂H₅ | 6-C₂H₅ | H | H | H | —CH₂—SCH₃ |
| C₂H₅ | 6-C₂H₅ | H | H | H | 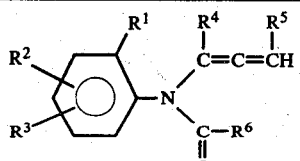 |
| C₂H₅ | 6-C₂H₅ | H | H | H | —CH=CH₂ |
| C₂H₅ | 6-C₂H₅ | H | CH₃ | H | 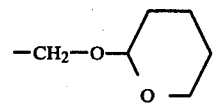 |
| C₂H₅ | 6-C₂H₅ | H | CH₃ | H | —CH₂—OCH₃ |
| C₂H₅ | 6-C₂H₅ | H | CH₃ | H | 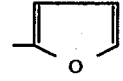 |
| C₂H₅ | 6-C₂H₅ | H | CH₃ | H | 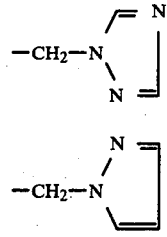 |
| C₂H₅ | 6-C₂H₅ | H | CH₃ | H | —CH₂—O—C₂H₅ |
| C₂H₅ | 6-C₂H₅ | H | CH₃ | H | —CH₂—O—SO₂CH₃ |
| C₂H₅ | 6-C₂H₅ | H | CH₃ | H | —CHCl₂ |
| C₂H₅ | 6-C₂H₅ | H | CH₃ | H | —COOCH₃ |
| C₂H₅ | 6-C₂H₅ | H | CH₃ | H | 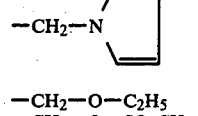 |
| C₂H₅ | 6-C₂H₅ | H | CH₃ | H | —CH₂—SCH₃ |
| C₂H₅ | 6-C₂H₅ | H | CH₃ | H | 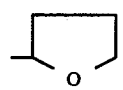 |
| C₂H₅ | 6-C₂H₅ | H | CH₃ | H | —CH=CH₂ |
| C₂H₅ | 6-C₂H₅ | H | H | CH₃ | 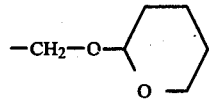 |
| C₂H₅ | 6-C₂H₅ | H | H | CH₃ | —CH₂—OCH₃ |
| C₂H₅ | 6-C₂H₅ | H | H | CH₃ | 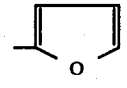 |
| C₂H₅ | 6-C₂H₅ | H | H | CH₃ | 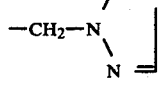 |
| C₂H₅ | 6-C₂H₅ | H | H | CH₃ | —CH₂—O—C₂H₅ |
| C₂H₅ | 6-C₂H₅ | H | H | CH₃ | —CH₂—O—SO₂CH₃ |
| C₂H₅ | 6-C₂H₅ | H | H | CH₃ | —CHCl₂ |

-continued $$\text{structure (I): } R^2\text{-phenyl ring with } R^1, R^3 \text{ substituents, N connected to } C(R^4)=C=CH(R^5) \text{ and } C(=O)R^6$$

| $R^1$ | $R^2$ | $R^3$ | $R^4$ | $R^5$ | $R^6$ |
|---|---|---|---|---|---|
| $C_2H_5$ | 6-$C_2H_5$ | H | H | $CH_3$ | —COOCH$_3$ |
| $C_2H_5$ | 6-$C_2H_5$ | H | H | $CH_3$ | tetrahydrofuran-2-yl |
| $C_2H_5$ | 6-$C_2H_5$ | H | H | $CH_3$ | —CH$_2$—SCH$_3$ |
| $C_2H_5$ | 6-$C_2H_5$ | H | H | $CH_3$ | —CH$_2$—O—(tetrahydropyran-2-yl) |
| $C_2H_5$ | 6-$C_2H_5$ | H | H | $CH_3$ | —CH=CH$_2$ |
| $C(CH_3)_3$ | H | H | H | H | tetrahydrofuran-2-yl |
| $C(CH_3)_3$ | H | H | H | H | —CH$_2$—OCH$_3$ |
| $C(CH_3)_3$ | H | H | H | H | —CH$_2$—N(1,2,4-triazol-1-yl) |
| $C(CH_3)_3$ | H | H | H | H | —CH$_2$—N(pyrazol-1-yl) |
| $C(CH_3)_3$ | H | H | H | H | —CH$_2$—O—C$_2$H$_5$ |
| $C(CH_3)_3$ | H | H | H | H | —CH$_2$—O—SO$_2$CH$_3$ |
| $C(CH_3)_3$ | H | H | H | H | —CHCl$_2$ |
| $C(CH_3)_3$ | H | H | H | H | —COOCH$_3$ |
| $C(CH_3)_3$ | H | H | H | H | tetrahydrofuran-2-yl |
| $C(CH_3)_3$ | H | H | H | H | —CH$_2$—SCH$_3$ |
| $C(CH_3)_3$ | H | H | H | H | —CH$_2$—O—(tetrahydropyran-2-yl) |
| $C(CH_3)_3$ | H | H | H | H | —CH=CH$_2$ |
| Cl | 6-CH$_3$ | H | H | H | tetrahydrofuran-2-yl |
| Cl | 6-CH$_3$ | H | H | H | —CH$_2$—OCH$_3$ |
| Cl | 6-CH$_3$ | H | H | H | —CH$_2$—N(1,2,4-triazol-1-yl) |
| Cl | 6-CH$_3$ | H | H | H | —CH$_2$—N(pyrazol-1-yl) |
| Cl | 6-CH$_3$ | H | H | H | —CH$_2$—O—C$_2$H$_5$ |
| Cl | 6-CH$_3$ | H | H | H | —CH$_2$—O—SO$_2$CH$_3$ |
| Cl | 6-CH$_3$ | H | H | H | —CHCl$_2$ |
| Cl | 6-CH$_3$ | H | H | H | —COOCH$_3$ |
| Cl | 6-CH$_3$ | H | H | H | tetrahydrofuran-2-yl |
| Cl | 6-CH$_3$ | H | H | H | —CH$_2$—SCH$_3$ |
| Cl | 6-CH$_3$ | H | H | H | —CH$_2$—O—(tetrahydropyran-2-yl) |
| Cl | 6-CH$_3$ | H | H | H | —CH=CH$_2$ |
| CH$_3$ | 3-CH$_3$ | 6-CH$_3$ | H | H | tetrahydrofuran-2-yl |
| CH$_3$ | 3-CH$_3$ | 6-CH$_3$ | H | H | —CH$_2$—OCH$_3$ |
| CH$_3$ | 3-CH$_3$ | 6-CH$_3$ | H | H | —CH$_2$—N(1,2,4-triazol-1-yl) |
| CH$_3$ | 3-CH$_3$ | 6-CH$_3$ | H | H | —CH$_2$—N(pyrazol-1-yl) |
| CH$_3$ | 3-CH$_3$ | 6-CH$_3$ | H | H | —CH$_2$—O—C$_2$H$_5$ |
| CH$_3$ | 3-CH$_3$ | 6-CH$_3$ | H | H | —CH$_2$—O—SO$_2$CH$_3$ |
| CH$_3$ | 3-CH$_3$ | 6-CH$_3$ | H | H | —CHCl$_2$ |
| CH$_3$ | 3-CH$_3$ | 6-CH$_3$ | H | H | —COOCH$_3$ |
| CH$_3$ | 3-CH$_3$ | 6-CH$_3$ | H | H | tetrahydrofuran-2-yl |
| CH$_3$ | 3-CH$_3$ | 6-CH$_3$ | H | H | —CH$_2$—SCH$_3$ |
| CH$_3$ | 3-CH$_3$ | 6-CH$_3$ | H | H | —CH$_2$—O—(tetrahydropyran-2-yl) |
| CH$_3$ | 3-CH$_3$ | 6-CH$_3$ | H | H | —CH=CH$_2$ |

The invention also provides a process for the preparation of an N-allenyl-acetanilide of the formula (I) in which an N-propargyl-acetanilide of the general formula

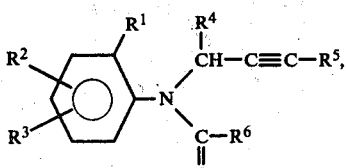

in which
R¹ to R⁶ have the meanings indicated above, is subjected to a rearrangement reaction in the presence of a base, as a catalyst, and if appropriate in the presence of a diluent.

If, for example, 2,6-dimethyl-N-(2-furoyl)-N-propargyl-aniline is used as the starting material and potassium tert.-butylate is used as the base, the course of the reaction can be represented by the following

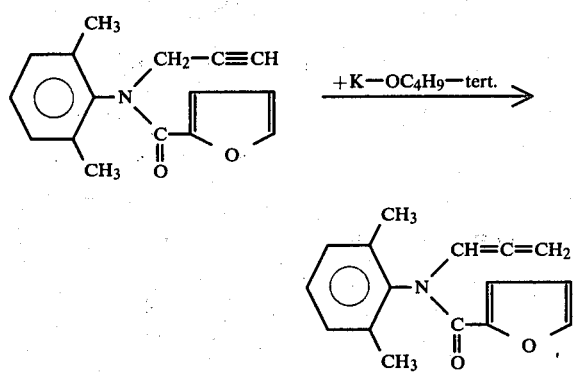

The formula (II) provides a general definition of the N-propargylacetanilides required as starting materials in carrying out the process according to the invention. In this formula, R¹, R², R³, R⁴, R⁵ and R⁶ preferably have those meanings which have already been mentioned as preferred in connection with the description of the compounds of the formula (I).

The N-propargyl-acetanilides of the formula (II) have not hitherto been described in the literature; however, they are the subject of U.S. Patent application No. 83,875, abandoned.

The N-propargyl-acetanilides of the formula (II) can be obtained by the process described therein, for example by a procedure in which (a) propargyl-anilines of the general formula

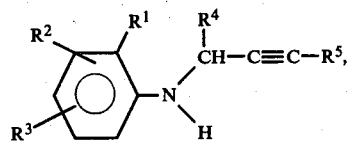

in which,
R¹ to R⁵ have the meanings indicated above, are reacted with acid chlorides, bromides or anhydrides of the formula

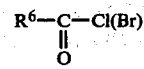 (IVa)

or $$(R^6-\underset{\underset{O}{\|}}{C}-)_2O,$$ (IVb)

in which
R⁶ has the meaning indicated above, in the presence of an inert solvent, for example tetrahydrofuran, and if appropriate in the presence of an acid-binding agent, for example triethylamine or pyridine, at a temperature between 20° and 100° C., or (b) anilides of the general formula

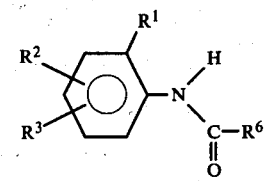

in which
R¹, R², R³ and R⁶ have the meanings indicated above, are reacted with propargyl halides of the general formula $$Hal-\underset{R^4}{\underset{|}{CH}}-C\equiv C-R^5,$$ (VI)

in which
R⁴ and R⁵ have the meanings indicated above and
Hal represents chlorine or bromine, preferably in an aqueous-organic two-phase system, for example aqueous sodium hydroxide solution or potassium hydroxide solution/toluene or methylene chloride, if appropriate with the addition of 0.1-1 mole of phase transfer catalyst, for example triethyl-benzyl-ammonium chloride, at a temperature between −20° and +80° C.

N-Propargyl-anilines of the formula (III) are known (see U.S. Pat. Nos. 3,535,377 and 4,001,325); they can all be obtained by known processes, for example by reacting corresponding anilines with propargyl halides of the formula (VI) or the corresponding propargyl sulphones, for example mesylates or tosylates, in the presence of an acid-binding agent, for example sodium carbonate or potassium carbonate, if appropriate in the presence of an inert organic solvent, for example ethanol, at a temperature between 20° and 150° C., it also being possible, preferably, to employ an excess of aniline.

N-Propargyl-anilines of the formula (III) in which R⁴ represents methyl can also be obtained by reacting the corresponding anilines with acetylene in the presence of copper acetylide under pressure (in this context, see Liebigs Ann, Chem. 596, 1 (1955)).

The anilides of the formula (V) can be obtained in a generally known manner, by reacting corresponding anilines with an acid chloride, bromide or anhydride of the formula (IVa) or (IVb) under the conditions of process (a) above, in the presence of an inert organic solvent, for example toluene or methylene chloride, if appropriate in the presence of an acid-binding agent, for example potassium carbonate or triethylamine, or in the presence of a catalyst, for example dimethylformamide, at a temperature between 0° and 100° C.

The acid chlorides, bromides and anhydrides of the formulae (IVa) and (IVb) and the propargyl halides of the formula (VI) are generally known compounds of organic chemistry.

Examples which may be mentioned of the N-propargylacetanilides of the formula (II) to be used as starting materials for the process according to the invention are:

(II)

| R¹ | R² | R³ | R⁴ | R⁵ | R⁶ | Melting point (°C.) |
|---|---|---|---|---|---|---|
| CH₃ | 6-CH₃ | H | H | H |  | 109–12 |
| CH₃ | 6-CH₃ | H | H | H | —CH₂—O—CH₃ | 49–51 |
| C₂H₅ | 6-C₂H₅ | H | H | H |  | 129–31 |
| CH₃ | 6-C₂H₅ | H | H | H |  | 129–31 |
| CH₃ | 6-CH₃ | H | H | CH₃ |  | 110–12 |
| CH₃ | 6-CH₃ | H | H | H |  | 120–21 |
| CH₃ | 6-CH₃ | H | H | H |  | 137–40 |
| CH₃ | 6-C₂H₅ | H | H | H |  | 88 |
| CH₃ | 6-CH₃ | H | H | CH₃ | —CH₂OCH₃ | $n_D^{20}$: 1,5362 boiling point: 125/0.1 mbar |
| C₂H₅ | 6-C₂H₅ | H | H | H | —CH₂OCH₃ | 74 |
| CH₃ | 6-CH₃ | H | H | H | —CHCl₂ | 114–15 |
| C₂H₅ | 6-CH₃ | H | H | H |  | 98–99 |
| Cl | 6-CH₃ | H | H | H | —CH₂OCH₃ | 80 |

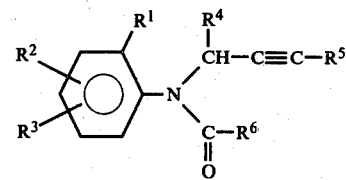

(II)

| R¹ | R² | R³ | R⁴ | R⁵ | R⁶ | Melting point (°C.) |
|---|---|---|---|---|---|---|
| CH₃ | 6-CH₃ | H | H | H | 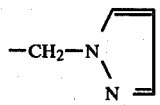 | 93–94 |

Preferred diluents for the reaction according to the invention are inert organic solvents. These include, as preferences, ethers, such as tetrahydrofuran or dioxane; alcohols, such as methanol, ethanol or tert.-butanol; and dimethylsulphoxide.

The process according to the invention is carried out in the presence of a base, as a catalyst. Bases which are preferably used here are alkali metal hydroxides or alkali metal carbonates, for example sodium hydroxide or carbonate or potassium hydroxide or carbonate, and especially alkali metal alcoholates, for example sodium methylate, sodium ethylate or potassium tert.-butylate.

The reaction temperatures can be varied within a substantial range in carrying out the process according to the invention. In general, the process is carried out at from 0° to 120° C., preferably from 20° to 80° C.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants of vegetative propagation stock and seeds, and of the soil.

As plant protection agents, the active compounds according to the invention can be used with particularly good success for combating Oomycetes, for example the pathogen of blight and brown rot of tomato and potato (Phytophthora infestans). It should be particularly emphasized that the active compounds according to the invention develop not only a protective action but also a curative/eradicative action. They also have systemic properties. Thus, it is possible to protect plants against fungal attack when the active compound is fed to the above-ground parts of the plant via the soil and the roots or via the seed.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents incude, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellants, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They can be used in the customary manner, for example by watering, immersion, spraying atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of, in general, 0.001 to 50 g, preferably 0.01 to 10 g, are generally employed per kilogram of seed.

For the treatment of soil, active compound concentrations of, in general, 0.00001 to 0.1% by weight, preferably 0.0001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

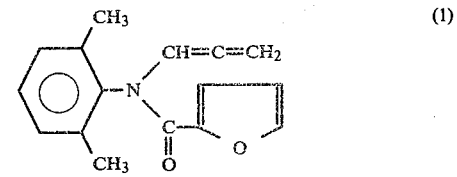
(1)

50 g (0.2 mol) of 2,6-dimethyl-N-(2-furoyl)-N-propargyl-aniline were dissolved in 200 ml of anhydrous tetrahydrofuran, and 150 mg of potassium tert.-butylate were added. During this procedure, the temperature of the solution rose to about 50° C., the solution becoming colored. The reaction mixture was left to stand for 2 hours and then poured onto 500 ml of water. The crystalline product which had precipitated was filtered off, dried and recrystallized from ethyl acetate/petroleum ether. 24 g (48% of theory) of 2,6-dimethyl-N-allenyl-N-(2-furoyl)-aniline of melting point 138°–41° C. were obtained. (The $^1$H-NMR spectrum indicated complete isomerization.)

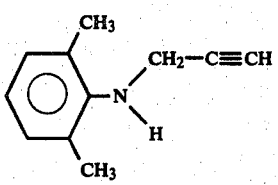

(a)

2,6-Dimethyl-N-propargyl-aniline was prepared by reacting 2,6-dimethyl-aniline with propargyl bromide according to the statements in the literature (see U.S. Patent Specification 4,001,325).

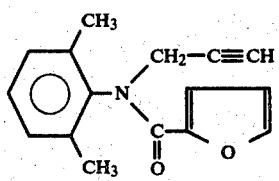

(b)

15.9 g (0.1 mol) of 2,6-dimethyl-N-propargylaniline and 8 g (0.1 mol) of pyridine were heated to the boil in 100 ml of tetrahydrofuran, and 13 g (0.1 mol) of furan-2-carboxylic acid chloride were added carefully. The reaction mixture was stirred under reflux for 15 minutes and then concentrated by distilling off the solvent in vacuo. The residue was taken up in methylene chloride and the methylene chloride mixture was washed with water. The organic phase was separated off, dried over sodium sulphate and concentrated. After triturating with petroleum ether, the residue crystallized. 22.5 g (89% of theory) of 2,6-dimethyl-N-(2-furoyl)-N-propargyl-aniline of melting point 109°–112° C. were obtained.

The following compounds of the general formula

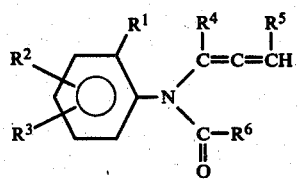

(I)

were obtained in analogous manner:

EXAMPLE 1.

| Compound No. | $R^1$ | $R^2$ | $R^3$ | $R^4$ | $R^5$ | $R^6$ | Melting point (°C.) |
|---|---|---|---|---|---|---|---|
| 2 | $CH_3$ | 6-$CH_3$ | H | H | H | —$CH_2OCH_3$ | 97–99 |
| 3 | $CH_3$ | 6-$CH_3$ | H | H | H | —$CH_2$—N⟨triazole⟩ | 117–19 |
| 4 | $CH_3$ | 6-$CH_3$ | H | H | H | isoxazolyl-$CH_3$ | 98–100 |
| 5 | Cl | 6-$CH_3$ | H | H | H | —$CH_2OCH_3$ | 95–100 |
| 6 | $CH_3$ | 6-$CH_3$ | H | H | H | —$CH_2OC_2H_5$ | 59–60 |

The fungicidal activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

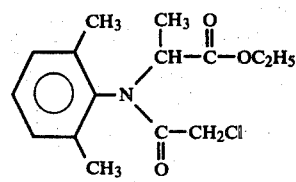

(A)

N-Chloroacetyl-N-(2,6-xylyl)-alanine ethyl ester

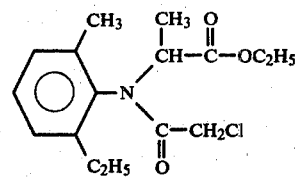

(B)

N-Chloroacetyl-N-(2-ethyl-6-methylphenyl)-alanine ethyl ester

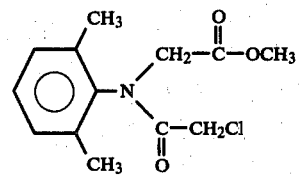

(C)

N-Chloracetyl-N-(2,6-xylyl)-glycine methyl ester

EXAMPLE A

Phytophthora test (tomato)/protective
Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated amount of emulsifier.

Young tomato plants with 2 to 4 foliage leaves were sprayed with the spray liquid until dripping wet. The plants remained in a greenhouse for 24 hours at 20 deg.C. and at a relative atmospheric humidity of 70%. The tomato plants were then inoculated with an aqueous spore suspension of Phytophthora infestans. The plants were brought into a moist chamber with an atmospheric humidity of 100% and a temperature of 18–20 deg.C.

After 5 days the infection of the tomato plants was determined. The assessment data were converted to percent infection: 0% meant no infection; 100% meant that the plants were totally infected.

In this test, for example, the following compounds exhibited a very good action which was significantly superior to that of the compounds (B) and (C) known from the prior art: compounds (1), (1) and (5).

EXAMPLE B

Phytophthora test (tomato)/systemic
Solvent: 4.7 parts by weight of acetone
Emulsifier: 0.3 part by weight of alkylaryl polyglycol ether
Water: 95 parts by weight The amount of active compound required for the desired concentration of the active compound in the watering liquid was mixed with the stated amount of solvent and the concentrate was diluted with the stated amount of water which contained the stated amount of the emulsifier.

Tomato plants grown in standard soil and having 2 to 4 foliage leaves were watered three times in the course of one week with 10 ml of the watering liquid, having the stated concentration of active compound, per 100 ml of soil.

The plants treated in this way were inoculated, after the treatment, with an aqueous spore suspension of *Phytophthora infestans*. The plants were brought into a humidity chamber at an atmospheric humidity of 100% and a temperature of 18 to 20 deg.C. After 5 days, the infection of the tomato plants was determined. The assessment data obtained were converted to percent infection. 0% denoted no infection and 100% denoted that the plants were totally infected.

In this test, for example, the following compound exhibited a very good action which was significantly superior to that of the compounds (A) and (B) known from the prior art: compound (1).

It will be appreciated that the instant specification and examples are set forth by way of illustration and not limitation, and that various modifications and changes may be made without departing from the spirit and scope of the present invention.

We claim:

1. An N-allenyl-acetanilide of the formula

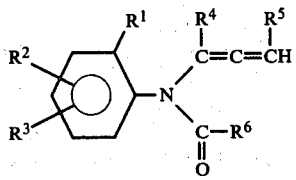

in which $R^1$ represents hydrogen, alkyl with up to 4 carbon atoms, or halogen, $R^2$ represents hydrogen or alkyl with up to 4 carbon atoms, $R^3$ represents hydrogen or alkyl with up to 4 carbon atoms, $R^4$ represents hydrogen or alkyl with up to 4 carbon atoms, $R^5$ represents hydrogen or alkyl with up to 4 carbon atoms, and $R^6$ represents alkyl, alkenyl or alkynyl, in each case optionally substituted by cyano or thiocyano; dihalogenoalkyl with 1 to 2 carbon atoms; or the grouping —$CH_2$—$OR^7$ or —$CH_2SR^7$, wherein $R^7$ represents an alkyl, alkenyl, alkynyl or alkoxyalkyl radical with up to 4 carbon atoms and optionally substituted by halogen, cyano or thiocyano.

2. A compound according to claim 1, wherein such compound is 2,6-dimethyl-N-allenyl-N-(methoxyacetyl)-aniline of the formula

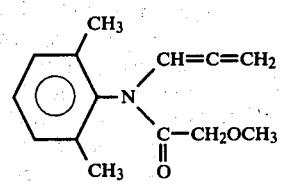

3. A compound according to claim 1, wherein such compound is 2-chloro-6-methyl-N-allenyl-N-(methoxyacetyl)-aniline of the formula

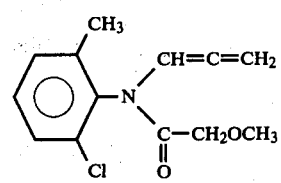

4. A fungicidal composition containing as active ingredient a fungicidally effective amount of a compound according to claim 1 in admixture with a diluent.

5. A method of combating fungi which comprises applying to the fungi, or to a habitat thereof, a fungicidally effective amount of a compound according to claim 1.

6. The method according to claim 5, in which said compound is 2,6-dimethyl-N-allenyl-N-(methoxyacetyl)-aniline, or 2-chloro-6-methyl-N-allenyl-N-(methoxyacetyl)-aniline.

* * * * *